United States Patent
Schaffner (10) Patent No.: US 7,322,823 B2
(45) Date of Patent: Jan. 29, 2008

(54) DENTAL MATRIX RETAINER

(76) Inventor: Alfred Schaffner, Strada Cantonale, CH-6805 Mezzovico (CH)

( * ) Notice: Subject to any disclaimer, the term of this patent is extended or adjusted under 35 U.S.C. 154(b) by 56 days.

(21) Appl. No.: 10/526,685

(22) PCT Filed: Sep. 3, 2003

(86) PCT No.: PCT/EP03/09741

§ 371 (c)(1),
(2), (4) Date: Mar. 3, 2005

(87) PCT Pub. No.: WO2004/021919

PCT Pub. Date: Mar. 18, 2004

(65) Prior Publication Data

US 2006/0003289 A1     Jan. 5, 2006

(30) Foreign Application Priority Data

Sep. 4, 2002 (DE) ................................ 102 40 683

(51) Int. Cl.
*A61C 5/04* (2006.01)
(52) U.S. Cl. ......................................... 433/155; 433/39
(58) Field of Classification Search ................ 433/155, 433/39
See application file for complete search history.

(56) References Cited

U.S. PATENT DOCUMENTS

| 3,383,769 A | 5/1968 | Davis |
| 3,795,981 A | 3/1974 | Franklin |
| 3,812,585 A | 5/1974 | Balson |
| 3,829,975 A | 8/1974 | Balson |
| 4,396,374 A * | 8/1983 | Ericson ....................... 433/39 |
| 4,824,365 A | 4/1989 | von Weissenfluh |
| 5,626,475 A * | 5/1997 | Von Weissenfluh et al. ........................ 433/155 |

FOREIGN PATENT DOCUMENTS

| DE | 645966 | 6/1937 |
| DE | 641005 | 12/1937 |
| DE | 19738189 | 2/1997 |
| EP | 0227590 | 1/1986 |
| EP | 0688540 | 6/1995 |
| EP | 0910996 | 10/1997 |

* cited by examiner

*Primary Examiner*—Cris L. Rodriguez
*Assistant Examiner*—Candice C Stokes
(74) *Attorney, Agent, or Firm*—Horst M. Kasper (57) ABSTRACT

The invention relates to a dental matrix retainer (1) used as an aid when filling two-surface cavities in the molars. It comprises a matrix holder (3) and a device for tensioning a matrix band (2) placed in the form of a loop (22) around the tooth which is to be treated, the matrix holder (3) being composed of a housing (5) with a circular opening (8), and of a spindle like inner body (9) which can turn in this opening (8) and which is provided with a gap (12).

The gap (12) can be aligned with a slit (10) in the wall of the housing (5) such that the superposed ends of the matrix band (2) can be inserted into this slit (10) and into the gap (12) aligned therewith and can be tensioned on the tooth by turning the spindle (9).

20 Claims, 5 Drawing Sheets

DENTAL MATRIX RETAINER

The invention relates to a dental matrix retainer used as an aid when filling two-surface cavities in the molars, with a matrix holder and a device for tensioning a matrix band placed in the form of a loop around the tooth which is to be treated, the matrix holder being composed of a housing with a circular opening, and of a spindle-like inner body which can turn in this opening and which is provided with a gap, said gap being able to be aligned with a slit in the wall of the housing such that the superposed ends of the matrix band can be inserted into this slit and into the gap aligned therewith and can be tensioned on the tooth by turning the inner body.

In dentistry, matrix retainers are used to ensure that a matrix band, placed around the patient's tooth which is to be filled, is drawn tight and that the filling then introduced into the drilled tooth is given shape and hold until the material has hardened.

According to EP 0 227 590 A1, a matrix retainer is made up of a sleeve with two wedge-shaped plates as clamping device protruding displaceably into the cavity of said sleeve. In the release position, when the plates for the most part protrude from the sleeve, their mutually facing surfaces are at a distance from one another so that the superposed ends of a matrix band can be pushed in. When the loop thus formed in the matrix band is placed around the tooth to be filled, it is drawn tight by pushing the sleeve by hand in the direction of the loop, whereupon the clamping plates close and are finally wedged in the sleeve.

According to U.S. Pat. No. 3,829,975, the superposed ends of a matrix band are held between two plates which are to be firmly connected to one another and are pushed into a separate clamping device and can be drawn in with the aid of a special tool. Serrated edges are provided on the narrow faces of the plates for the engagement of a latch which is located on the clamping device and is intended to prevent the matrix band from coming loose during subsequent treatment of the tooth. The production and handling of the device are complicated and time-consuming. The plates, with the ends of the matrix band secured in them, have to be connected to one another in an exact position since their teeth must be aligned precisely in relation to one another so that the latch provided on the clamping device can come into engagement. This requires a high level of precision in the production and assembling of the individual parts.

U.S. Pat. No. 4,824,365 describes a matrix band with tensioning device which remain permanently connected to one another. The tensioning device is composed of a ring made of a permanently deformable material. Lying opposite one another in this ring there are two slits through which the ends of the matrix band are guided. In the slit of the tensioning ring directed away from the loop of the matrix band, the matrix ends are connected firmly and permanently thereto. When the loop is placed around the tooth, tightening is obtained by lateral compression and permanent deformation of the tensioning ring, and its slit opposite the loop slides on the matrix band and thus narrows the loop. The matrix band accordingly has to be held on the tooth, during the subsequent treatment, by the tensioning ring alone and by the tension applied by its deformation. A really secure fit is thus not guaranteed.

A common feature of all these matrix retainers is that the tensioning procedure is carried out by displacing a tensioning or clamping means on the matrix band. This, however, cannot guarantee a secure and sufficiently tight fit of the matrix band on the tooth. Moreover, a disadvantage of some of the devices is that the dentist, when fitting and tensioning the matrix band, has to work with the fingers of both hands in the patient's mouth and thus blocks his view of the procedure or at least makes it difficult to monitor.

The matrix retainer described in DE 197 38 189 A1 is made in two parts and is composed of a wrench and a forceps-shaped matrix holder whose grip arms, at one end, are connected in an articulated manner to a bridge and a pre-shaped leaf spring which holds the grip arms open in the unstressed state. A screw is firmly connected to the bridge and projects through an opening in the leaf spring. At its free end, it can be gripped by the wrench and turned, as a result of which the leaf spring is compressed and the free ends of the grip arms on which a matrix band has been fixed beforehand are closed in a forceps movement. The wrench can initially be removed for the subsequent treatment and is only used again to release the matrix holder. Since the matrix holder only executes a gripping movement and does not exert any tension on the matrix band, the latter has to be fixed in exactly the right length on the ends of the grip arms in order to achieve a hold on the tooth. A sufficiently firm hold of the matrix band on the tooth is not guaranteed by the gripping movement.

According to EP 0 668 540 A1, a matrix retainer is composed of a ring in which a pin is arranged coaxially and is able to rotate. Both the ring and the pin are provided with a slit through which the superposed ends of a matrix band are guided. By turning the pin, the matrix band is drawn tight. The handling of the device is not particularly comfortable and requires skill; the dentist, when turning the pin, also has to work entirely within the patient's mouth so that the ring enclosing the pin bears directly and firmly on the tooth, the punctiform bearing of the ring on the tooth being unfavorable.

The object of the invention is to make available a matrix retainer with which a matrix band can be drawn tight around a tooth with extremely finely adjustable tensioning, and which matrix retainer is safe and comfortable to handle and, during the subsequent dental treatment, poses the least possible inconvenience or obstacle.

In the case of a matrix retainer of the type mentioned at the outset, this is achieved by the fact that a toothed wheel is provided on the end of the spindle protruding from the circular opening of the housing, said toothed wheel being able to be engaged with a drive device which has a laterally outwardly extended drive shaft.

The laterally outwardly extended drive for turning the spindle permits precise actuation of the matrix retainer outside the mouth. After placing the matrix retainer on the tooth, the dentist does not have to work inside the patient's mouth to obtain tensioning and is able to observe and control the tensioning procedure.

The toothed wheel at the upper end of the spindle is preferably a crown wheel which can be brought into engagement with a drive pinion belonging to the drive device, which drive pinion can be turned via the laterally outwardly extended drive shaft. With this drive mechanism, the matrix band can be tightened on the tooth very precisely and with exactly the right tensioning.

In its simplest embodiment, the drive device for the spindle is composed only of the drive shaft which, at one end, carries the drive pinion which can be engaged with the crown wheel so that, by turning the drive shaft, the spindle is turned inside the housing so as to tension the matrix band. If the drive pinion is slightly beveled at its front face, it can be better guided into the crown wheel.

According to an advantageous development of the drive device, the drive shaft can be rotated inside a tubular sleeve with the aid of a rotary knob provided at its end remote from the drive pinion, from which sleeve a support fork protrudes forward underneath the drive pinion and can slide under an edge protruding laterally from the upper end of the housing, and the drive pinion engaging with the crown wheel of the spindle. The drive device thus has a better hold on the matrix holder during the tensioning procedure.

As soon as the tensioning procedure is concluded, the drive device can be disengaged and set aside so that it does not get in the way of the subsequent dental treatment.

According to another embodiment, the drive device can be composed of a drive worm which engages with the toothed wheel of the spindle and which can be turned via the laterally outwardly extended drive shaft.

The matrix retainer according to the invention can be made inexpensively from plastic and can be produced preferably as a disposable article, so that all hygiene requirements are satisfied; it is thus also made very light, making its use convenient for the patient and the dentist. It is also conceivable, however, for only the matrix holder to be made as a disposable article and for the drive device to be reusable.

The invention is described in more detail below and by way of example with reference to the attached drawings, in which.

Figure 1:
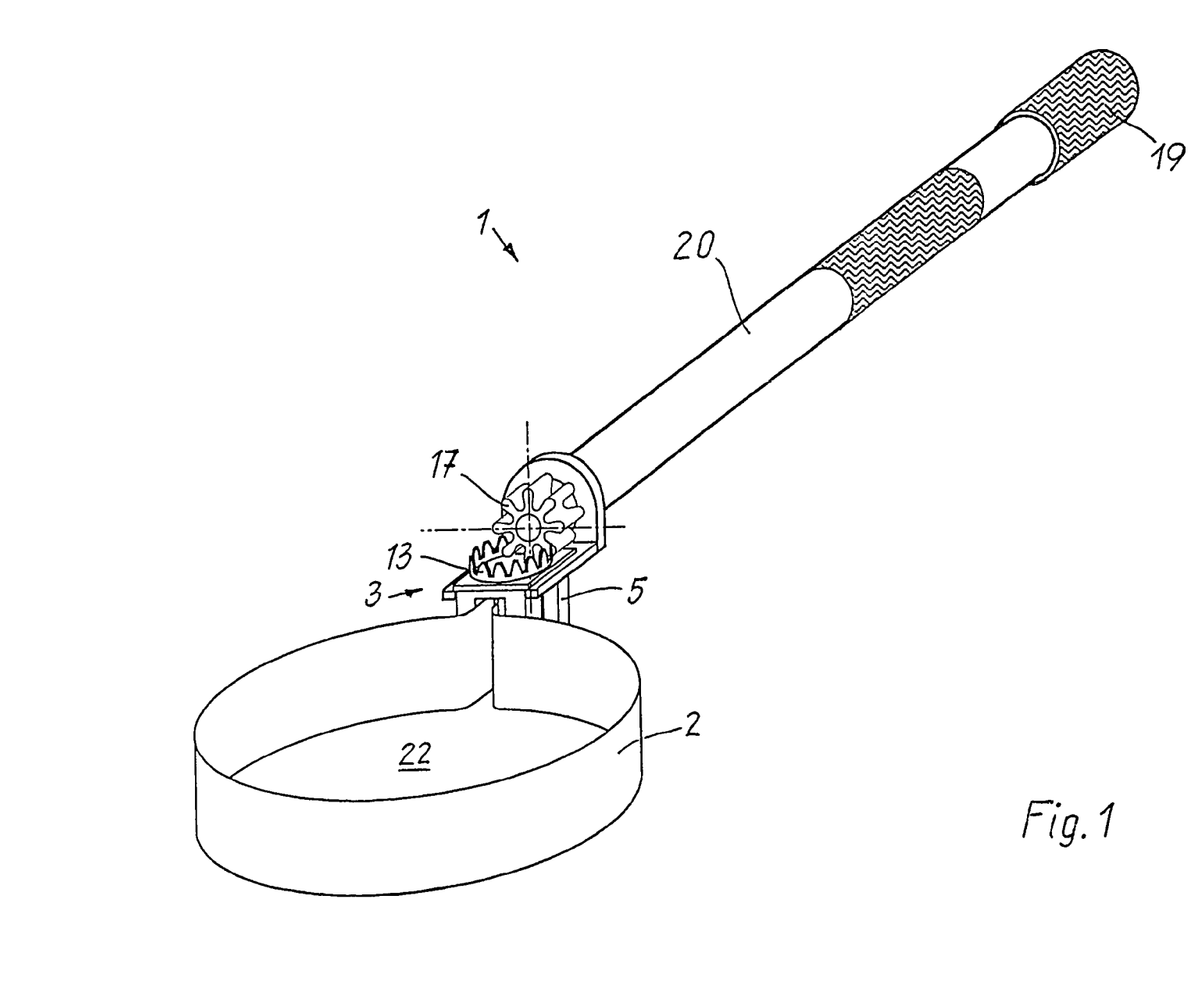
FIG. 1 shows a first preferred embodiment of a matrix retainer according to the invention, with inserted matrix band.
Figure 2:
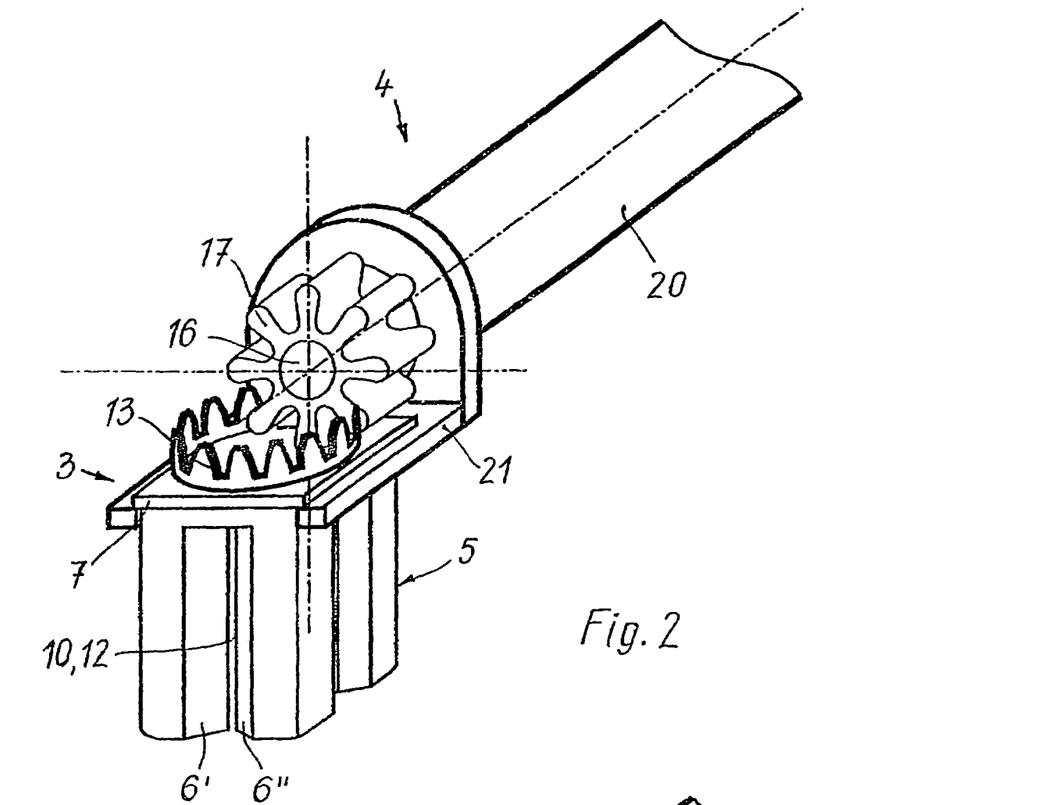
FIG. 2 shows an enlarged view of the head end of the matrix retainer according to FIG. 1, without matrix band.
Figure 3:
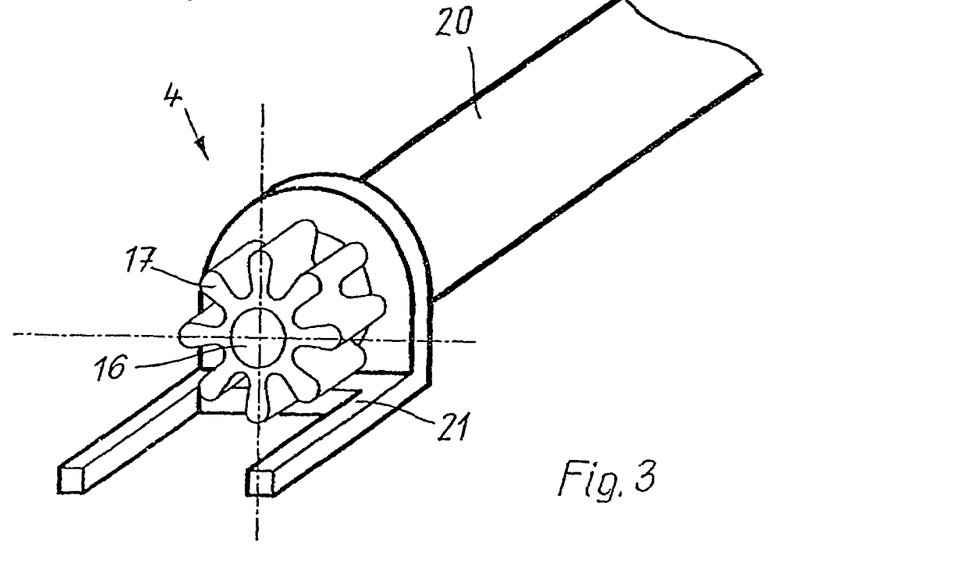
FIG. 3 shows the drive device of the matrix retainer according to FIG. 1.
Figures 4, 5:
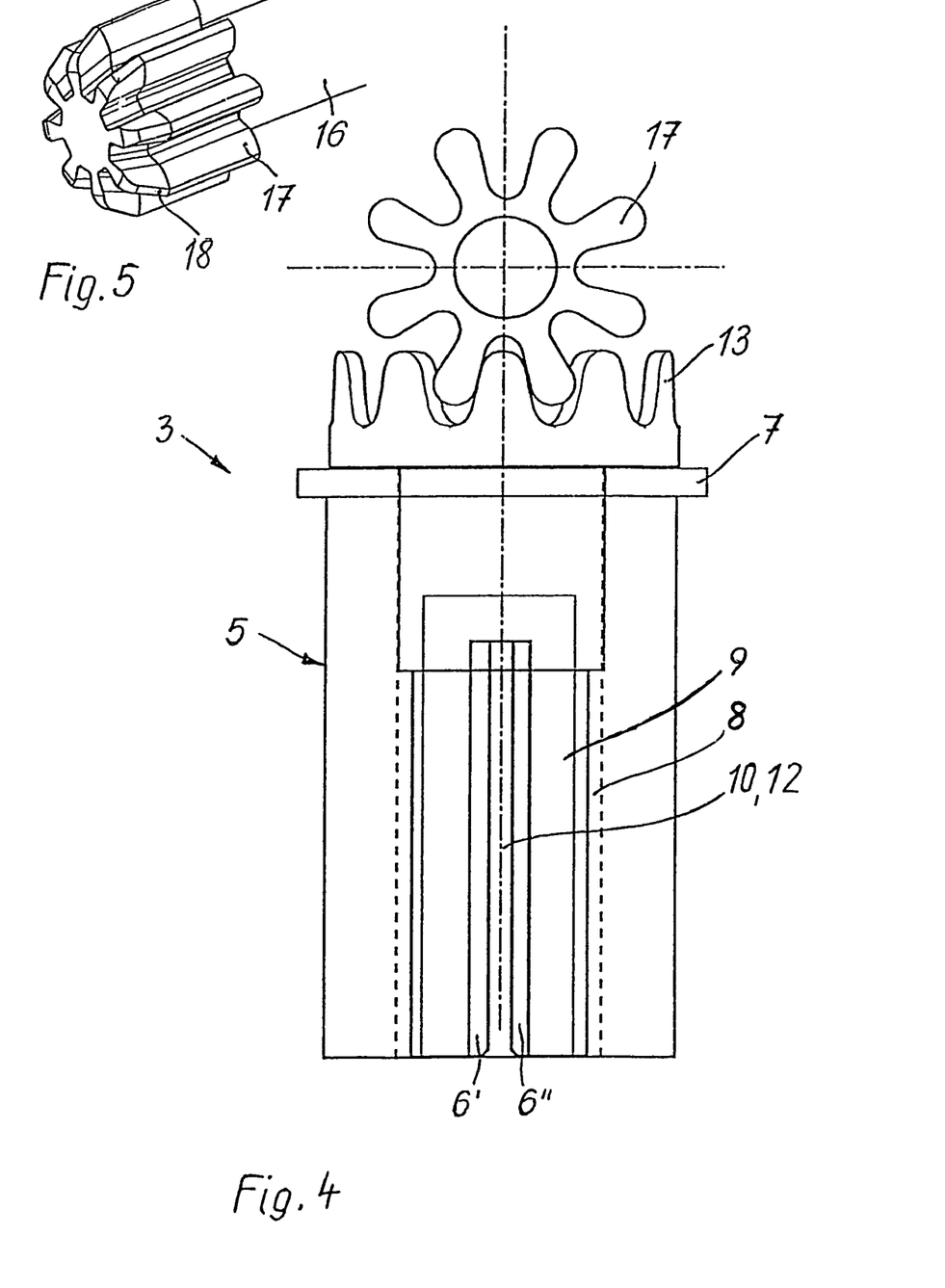
FIG. 4 shows a transparent front view of the matrix holder which is used in the matrix retainer according to FIG. 1 and engages with the drive device.
FIG. 5 shows a perspective view of the drive pinion.

FIG. 1 is a perspective representation of a preferred embodiment of the matrix retainer 1 according to the invention, with inserted matrix band 2. FIG. 2 shows, once again, the head end of said matrix retainer 1 in an enlarged representation, without matrix band. It is composed principally of a matrix holder 3 (see also FIG. 4) and of a drive device 4. As is known per se, the matrix holder 3 is composed of a housing 5 which, on its front face, has a vertically extending, preferably concavely curved bearing surface 6 for a tooth; the radius of the curve is suitably adapted and can advantageously measure ca. 2 mm. It has been found that it also suffices if the bearing surface 6 is formed by two bevels 6', 6" running toward one another and with a depth of ca. 2 mm.

Figure 6A:
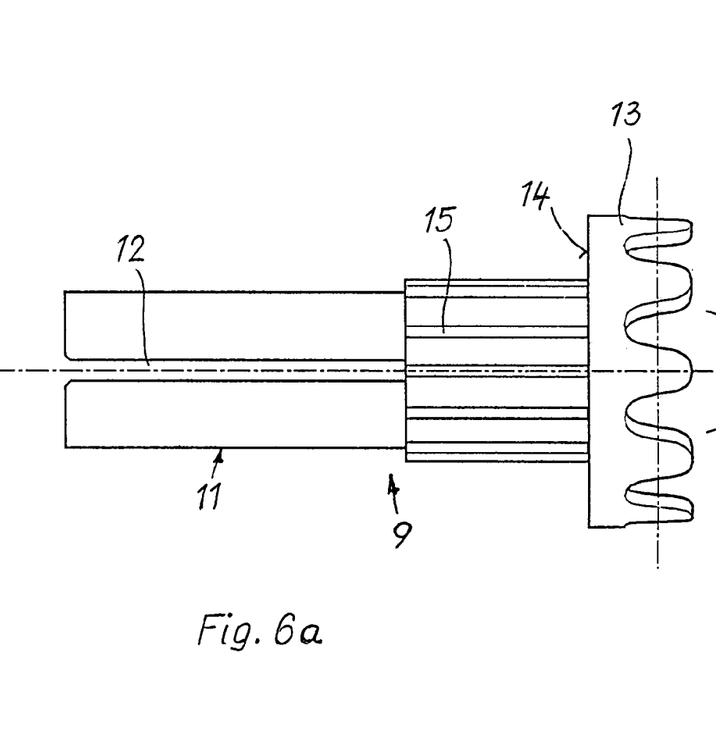
FIGS. 6, 6a and 6c show the spindle used in the matrix holder according to FIG. 4, in a side view, a bottom view and a stylized top view, respectively.
Figure 6B:
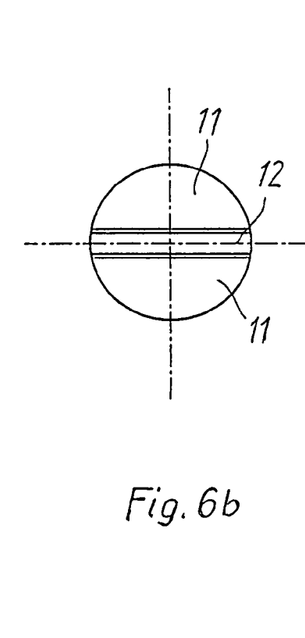
Figure 6C:
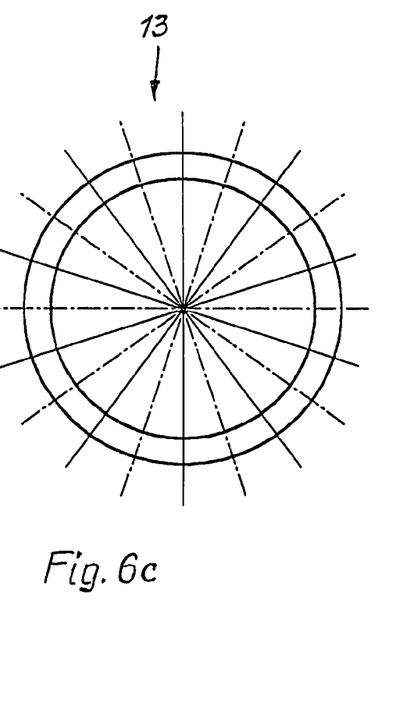

At its upper end, the housing 5 has an edge 7 protruding all round from it, and it has a central, vertically extending, circular opening 8 into which a spindle 9 (see FIGS. 6a through 6c) can be inserted. A vertical slit 10, open at the bottom, is provided in the wall with the bearing surface 6 and at the lowermost point of the bearing surface 6. According to FIGS. 6a through 6c, the spindle 9 has a cylindrical main body 11 which is halved along about ⅔ of its length to a deep gap 12 open at one end. At its end remote from the opening of the gap 12, the spindle 9 carries a crown wheel 13 which is set off by a step 14. When the spindle 9 is inserted into the circular opening 8 of the housing 5, its gap 12 can be aligned with the slit 10 in the housing wall. A portion of the spindle 9 between the gap 12 and the crown wheel 13 can advantageously be provided with a ribbing 15 which serves to adjust the torque so that the matrix band 2 cannot come loose when used as intended.

In its simplest embodiment, the drive device 4 is initially composed of a drive shaft 16 which, at one end, carries a drive pinion 17 which can be brought into engagement with the crown wheel 13 of the spindle 9. The drive pinion 17 is preferably conically beveled at its front face (see FIG. 5). This slight beveling 18 means that the drive pinion 17 can be better guided into the crown wheel 13.

According to the advantageous development shown in the figures, the drive shaft 16 can be turned inside a tubular sleeve 20 with the aid of a rotary knob 19 provided at its end remote from the drive pinion 17. From this sleeve 20, a support fork 21 protrudes forward underneath the drive pinion 17, with which support fork 21 the drive device 4 can be pushed under the edge 7 of the housing 5 of the matrix holder 3, the drive pinion 17 coming into engagement with the crown wheel 13 of the spindle 9.

To use the matrix retainer described here as an aid for placing a matrix band 2 with sufficient tensioning around a tooth which is to be treated, the ends of the matrix band 2 are superposed in a known manner and are together pushed through the slit 10 of the matrix holder and through the gap 12 of the spindle 9 aligned with the slit 10, as can be seen from FIG. 1. The bevels 6', 6" of the bearing surface 6 which run in toward the slit 10 facilitate the insertion of the matrix band 2. The matrix band 2 thus forms a round loop 22 which is pushed over the tooth in question. The drive pinion 17 is now introduced into the crown wheel 13 of the spindle 9 and the latter is turned about its own axis in the housing 5 by turning of the drive shaft 16. Thus, the matrix band 2 is drawn through the slit 10 and the gap 12 into the tensioner and wound about the spindle 9, so that the loop 22 draws together and the matrix band 2 is placed tightly around the tooth. The width of the loop 22, or the tensioning with which the matrix band 2 is placed around the tooth, can be controlled and adjusted very precisely by actuation of the drive shaft 16. Spontaneous loosening of the matrix band 2 during the subsequent treatment is not possible, and it is prevented in particular by the abovementioned ribbing 15 on the spindle 9.

After the matrix band 2 has been drawn tight around the tooth, the drive device 4 can be disengaged from the crown wheel 13 and set aside, so that it does not get in the way of the subsequent treatment. Thus, only the matrix holder 3 and matrix band 2 remain in the patient's mouth for the duration of the subsequent treatment.

The housing 5 and spindle 9 of the matrix holder 3 are preferably designed as disposable articles and are discarded after treatment together with the matrix band 2. The drive device 4 can be reusable, if so desired.

Figure 7:
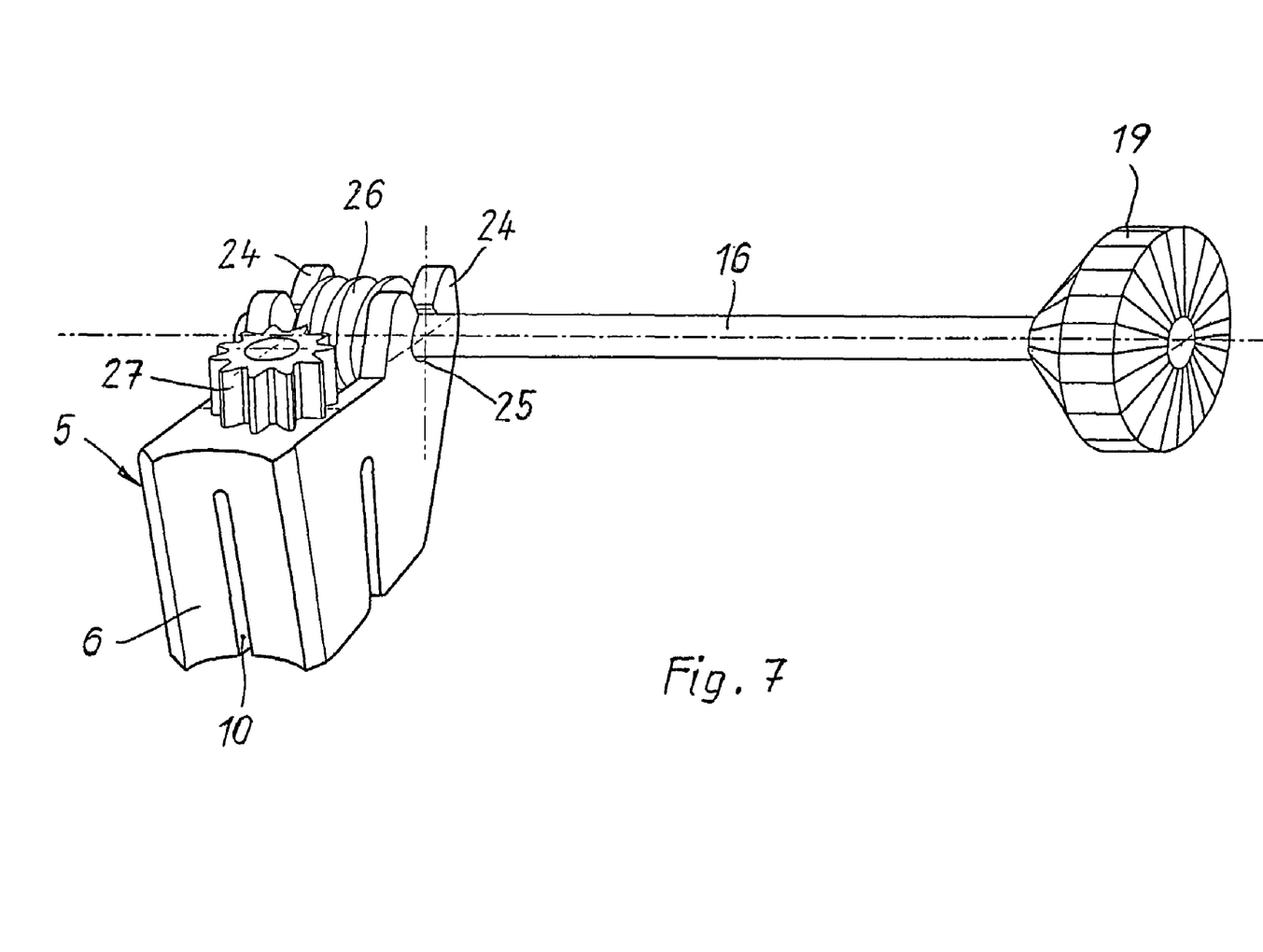
FIG. 7 shows a second embodiment of the matrix retainer according to the invention.

FIG. 7 shows an embodiment of the matrix retainer 1 in which the drive device 4 is designed as a worm gear 23. Wing-like extensions 24 running rearward and upward are formed on that side of the housing 5 directed away from the bearing surface 6, and circular recesses 25 open at the top are provided as bearings for the drive shaft 16 of a drive worm 26. The drive worm 26 comes to lie between the bearings formed on the extensions 24 and is brought into engagement with a toothed wheel 27 fitted on the spindle 9. The function is otherwise the same as that described above.

LIST OF REFERENCE NUMBERS

| | |
|---|---|
| 1 | matrix retainer |
| 2 | matrix band |
| 3 | matrix holder |
| 4 | drive device |
| 5 | housing |
| 6 | bearing surface |
| 6', 6" | bevels |
| 7 | edge |
| 8 | opening |
| 9 | spindle |
| 10 | slit |
| 11 | main body |
| 12 | gap |
| 13 | crown wheel |
| 14 | step |
| 15 | ribbing |
| 16 | drive shaft |
| 17 | drive pinion |
| 18 | beveling |
| 19 | rotary knob |
| 20 | sleeve |
| 21 | support fork |
| 22 | loop |
| 23 | worm gear |
| 24 | extensions |
| 25 | recesses |
| 26 | drive worm |
| 27 | toothed wheel |

The invention claim is:

1. A dental matrix retainer used as an aid when filling two-surface cavities in the molars, with a matrix holder (3) and a device for tensioning a matrix band (2) placed in the form of a loop (22) around the tooth which is to be treated, the matrix holder (3) being composed of a housing (5) with a circular opening (8), and of a ~inner body (9) which can turn in this opening (8) and which is provided with a gap (12), said gap (12) being able to be aligned with a slit (10) in the wall of the housing (5) such that the superposed ends of the matrix band (2) can be inserted into this slit (10) and into the gap (12) aligned therewith and can be tensioned on the tooth by turning the inner body (9), characterized in that a toothed wheel (13, 27) is provided on the upper end of the inner body (9) protruding from the circular opening (8) of the housing (5), said toothed wheel (13, 27) being able to be engaged immediately and to contact directly with a drive device (4) which has a laterally outwardly extended drive shaft (16), wherein the drive shaft (16) can be turned inside a tubular sleeve (20) with the aid of a rotary knob (19) provided at an end of the drive shaft (16) disposed remote from the drive pinion (17), wherein a support fork (21) protrudes forward underneath the drive pinion (17) and from the tubular sleeve (20) and can slide under an edge (7) protruding laterally from the upper end of the housing (5).

2. The matrix retainer as claimed in claim 1, characterized in that the toothed wheel at the upper end of the inner body (9) is a crown wheel (13) which can be brought into proximate engagement with a drive pinion (17) belonging to the drive device (4), which drive pinion (17) can be turned via the laterally outwardly extended drive shaft (16).

3. The matrix retainer as claimed in claim 2, characterized in that the drive pinion (17) is slightly beveled at its front face.

4. The matrix retainer as claimed in claim 1, characterized in that the drive device (4) is composed of the drive shaft (16) and of the drive pinion (17) arranged at one end thereof.

5. The matrix retainer as claimed in claim 1, characterized in that the matrix retainer is composed of two parts and comprises a matrix holder (3) and a separate drive device (4) attachable from a side to the matrix holder (3) and again disengageable from the matrix holder (3), wherein the drive device (4) includes a laterally outwardly extended drive shaft (16) and a drive pinion (17) disposed at an end of this drive shaft (16), wherein the drive pinion (17) can be engaged and disengaged with a crown wheel (13) of the inner body (9), and wherein the crown wheel (13) of the inner body (9) upwardly protrudes from the housing (5) of the matrix holder (3).

6. A matrix retainer used as an aid when filling two-surface cavities in the molars, with a matrix holder (3) and a device for tensioning a matrix band (2) placed in the form of a loop (22) around the tooth which is to be treated, the matrix holder (3) being composed of a housing (5) with a circular opening (8), and of a inner body (9) which can turn in this opening (8) and which is provided with a gap (12), said gap (12) being able to be aligned with a slit (10) in the wall of the housing (5) such that the superposed ends of the matrix band (2) can be inserted into this slit (10) and into the gap (12) aligned therewith and can be tensioned on the tooth by turning the inner body (9), characterized in that a toothed wheel (13, 27) is provided on the upper end of the inner body (9) protruding from the circular opening (8) of the housing (5), said toothed wheel (13, 27) being able to be engaged with a drive device (4) which has a laterally outwardly extended drive shaft (16), wherein the drive device (4) is composed of a drive worm (26) which engages with the toothed wheel (27) of the spindle (9) and which can be turned via a laterally outwardly extended drive shaft (16).

7. A dental matrix retainer used as an aid when filling two-surface cavities in the molars, comprising a matrix holder (3) and a drive device (4) connectable and again disengageable with the matrix holder (3) for tensioning of a matrix band (2) placed like a loop (22) around a tooth which is to be treated the matrix holder (3) being composed of a housing (5) with a circular opening (8), and of a inner body (9) which can turn in this opening (8) and which is provided with a gap (12), said gap (12) being able to be aligned with a slit (10) in the wall of the housing (5) such that the superposed ends of the matrix band (2) can be inserted into this slit (10) and into the gap (12) aligned therewith and can be tensioned on the tooth by turning the inner body (9), wherein a drive pinion (17) furnished at an end of a rotatable drive shaft (16) is bringable into engagement with a toothed wheel (13, 27) provided on the upper end of the inner body (9) protruding from the circular opening (8) of the housing (5), characterized in that the drive shaft (16) is rotatable within a tubular sleeve (20), wherein a support fork (21) projects in a front of the tubular sleeve (20) below the drive pinion (17), wherein the support fork (21) is disposed slidable under an edge (7) protruding from all sides at the housing (5) of the matrix holder (3), and wherein thereby the drive pinion (17) of the drive shaft (16) engages directly with the toothed wheel (13, 27) at the inner body (9) of the matrix holder (3).

8. The matrix retainer as claimed in claim 7, characterized in that the toothed wheel at the upper end of the inner body (9) is a crown wheel (13).

9. The matrix retainer as claimed in claim 7, characterized in that the drive pinion (17) is slightly beveled at its front face.

10. The matrix retainer as claimed in claim 7, characterized in that the drive shaft (16) can be turned inside a tubular sleeve (20) with the aid of a rotary knob (19) provided at an end of the drive shaft (16) disposed remote from the drive pinion (17).

11. The matrix retainer as claimed in claim 7, characterized in that
the drive device (4) is composed of a drive worm (26) which engages with the toothed wheel (27) of the spindle (9) and which can be turned via a laterally outwardly extended drive shaft (16).

12. A dental matrix retainer used as an aid when filling two-surface cavities in the molars, comprising
a housing (5) having a wall, having a circular opening (8), and having a slit (10) in the wall;
a first edge (7) protruding laterally from an upper end of the housing (5);
a second edge (7) protruding laterally from an upper end of the housing (5),
wherein the second edge (7) is disposed parallel to the first edge (7);
a inner body (9) rotatable in this circular opening (8) and which inner body (9) is provided with a gap (12), said gap (12) being able to be aligned with the slit (10) in the wall of the housing (5) such that superposed ends of a matrix band (2) are insertable into this slit (10) and into the gap (12) aligned with the slit (10) and said matrix band (2) is tensionable on a tooth of a dental patient by turning the inner body (9);
a toothed wheel (13, 27) provided on an upper end of the inner body (9) protruding from the circular opening (8) of the housing (5),
wherein the housing (5), the edge (7) protruding from all sides at the housing (5), the inner body (9), and the toothed wheel (13, 27) form a matrix holder (3);
a rotatable drive shaft (16);
a drive pinion (17) furnished at an end of the rotatable drive shaft (16) and bringable into engagement with the toothed wheel (13, 27) provided on the upper end of the inner body (9) protruding from the circular opening (8) of the housing (5);
a tubular sleeve (20) surrounding the rotatable drive shaft (16) and wherein the rotatable drive shaft (16) is rotatable within the tubular sleeve (20);
a support fork (21) projecting in a front of the tubular sleeve (20) below the drive pinion (17), wherein the support fork (21) is disposed slidable under the first edge (7) and under the second edge (7) protruding from two opposite sides at the housing (5), and wherein thereby the drive pinion (17) of the drive shaft (16) engages directly with the toothed wheel (13) at the inner body (9),
wherein the rotatable drive shaft (16), the drive pinion (17), the tubular sleeve (20), and the support fork (21) form a drive device (4),
wherein the matrix holder (3) and the drive device (4) are connectable and again disengageable from the matrix holder (3) for tensioning of the matrix band (2) placed like a loop (22) around the tooth of a dental patient, which tooth is to be treated.

13. The matrix retainer as claimed in claim 12, wherein the toothed wheel at the upper end of the inner body (9) is a crown wheel (12); and
wherein an axis of the drive shaft (16) intersects with an axis of the crown wheel at a right angle.

14. The matrix retainer as claimed in claim 13, wherein the drive pinion (17) is slightly conically beveled at its front face, such that the drive pinion (17) is better guidable into engagement with the crown wheel (13).

15. The matrix retainer as claimed in claim 12 further comprising
a rotary knob (19) provided at a second end of the drive shaft (16) disposed remote from the drive pinion (17), wherein the rotary knob turns the drive shaft (16) inside the tubular sleeve (20).

16. The matrix retainer as claimed in claim 12 further comprising
a ribbing (15) furnished on the inner body (9) between the gap (12) and the toothed wheel (13, 27), wherein the ribbing (15) serves to adjust the torque so that the matrix band cannot come loose when used as intended.

17. The matrix retainer as claimed in claim 12 further comprising
a rotary knob (19) attached to a second end of the drive shaft (16) for turning the drive shaft (16) inside the tubular sleeve (20);
wherein the support fork (21) protrudes forward underneath the drive pinion (17) from the sleeve (20), wherein the drive device (4) is pushable with the support fork (21) under the edge (7) of the housing (5) of the matrix holder (3) and wherein the drive pinion (17) comes into engagement with the toothed wheel (13) of the inner body (9).

18. The matrix retainer as claimed in claim 12 wherein the support fork (21) has two tines, wherein the two tines extend in a direction parallel to the drive shaft (16), wherein the two tines have a rectangular cross-section, wherein each tine is furnished as a straight bar, and wherein the support fork is disposed at a height level located below a lower periphery of a motion of the drive pinion (17).

19. The matrix retainer as claimed in claim 18 further comprising a third edge (7) protruding in a front from the upper end of the housing (5);
a fourth edge (7) protruding in a rear from the upper end of the housing (5), wherein the fourth edge (7) is disposed parallel to the third edge (7); and
wherein the third edge (7) and the fourth edge (7) are disposed perpendicular to the first edge (7) and to the second edge (7), wherein the edges (7) all have the same length;
wherein a distance between the two tines is smaller than an outer distance between the first edge (7) and the second edge (7) and is larger than the outer diameter of the housing (5) immediately below the first edge (7) and the second edge (7);
wherein the housing (5) has a fourfold rotation axis and wherein two mirror planes of the housing (5) contain the fourfold rotation axis; wherein the housing contains three additional vertical slits (10); wherein each vertical slit (10) is furnished with two bevels (6', 6") on the outside of the housing (5).

20. A dental matrix retainer used as an aid when filling two-surface cavities in the molars, comprising
a housing (5) having a wall, having a circular opening (8), and having a slit (10) in the wall;
an edge (7) protruding from all sides at the housing (5);
a inner body (9) rotatable in this circular opening (8) and which inner body (9) is provided with a gap (12), said gap (12) being able to be aligned with the slit (10) in the wall of the housing (5) such that superposed ends of a matrix band (2) are insertable into this slit (10) and into the gap (12) aligned with the slit (10) and said matrix band (2) is tensionable on a tooth of a dental patient by turning the inner body (9);

a toothed wheel (13, 27) provided on an upper end of the inner body (9) protruding from the circular opening (8) of the housing (5), wherein the housing (5), the edge (7) protruding from all sides at the housing (5), the inner body (9), and the toothed wheel (13, 27) form a matrix holder (3);

a laterally, outwardly extended rotatable drive shaft (16);

a drive worm (17) furnished at an end of the rotatable drive shaft (16) and bringable into engagement with the toothed wheel (13, 27) provided on the upper end of the inner body (9) protruding from the circular opening (8) of the housing (5);

wherein the rotatable drive shaft (16), and the drive worm (26) form a drive device (4), wherein the matrix holder (3) and the drive device (4) are connectable and again disengageable from the matrix holder (3) for tensioning of the matrix band (2) placed like a loop (22) around the tooth of a dental patient, which tooth is to be treated.

* * * * *